United States Patent
Miyake et al.

(10) Patent No.: US 9,969,671 B2
(45) Date of Patent: May 15, 2018

(54) METHOD FOR PRODUCING ETHYL 4-METHYLOCTANOATE

(71) Applicant: SHIN-ETSU CHEMICAL CO., LTD., Chiyoda-ku, Tokyo (JP)

(72) Inventors: Yuki Miyake, Joetsu (JP); Yusuke Nagae, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days. days.

(21) Appl. No.: 15/453,414

(22) Filed: Mar. 8, 2017

(65) Prior Publication Data

US 2017/0267625 A1    Sep. 21, 2017

(30) Foreign Application Priority Data

Mar. 16, 2016 (JP) ................................ 2016-052500

(51) Int. Cl.
    *C07C 67/10* (2006.01)
    *C07C 67/32* (2006.01)

(52) U.S. Cl.
    CPC .................................... *C07C 67/32* (2013.01)

(58) Field of Classification Search
    None
    See application file for complete search history.

(56) References Cited

PUBLICATIONS

Taguri et al. Tetrahedron Asymmetry 23 (2012) 852-858.*
Randad et al. Indian Journal of Chemistry, vo. 25 B, 1986, 296-298.*
McMurry, Organic Chemistry Textbook, 2011, Science, p. 882-884.*
Krapcho, Organic Reactions, vol. 81, 2013, John Wiley & Sons, Inc.1-334.*
Valentine Rougoussis, et al., Efficient Synthesis of (±) Methyloctanoic Acid, Aggregation Pheromone of Rhinoceros Beetles of the Genus *Oryctes* (Coleoptera: Dyanstidae, Scarabaeidae), Journal of Agricultural and Food Chemistry, 2007, Vol. 55, pp. 5050-5052, published on the web May 24, 2007.
Rebecca H. Hallett, et al.,Aggregation Pheromone of Coconut Rhinoceros Beetle, *Oryctes rhinoceros* (L.) (Coleoptera: Scarabaeidae), Journal of Chemical Ecology, 1995, vol. 21 No. 10, pp. 1549-1570, Plenum Publishing.
G. Gries, et al., Aggregation Pheromone of the African Rhinoceros Beetle, *Oryctes monoceros* (Olivier) (Coleoptera: Scarabaeidae), Department of Biological Sciences, 2013, pp. 363-366, Verlag Zeitschrift.

* cited by examiner

*Primary Examiner* — Sudhakar Katakam
*Assistant Examiner* — Ana Z Muresan
(74) *Attorney, Agent, or Firm* — Williams Mullen; F. Michael Sajovec

(57) ABSTRACT

There is provided a method for producing ethyl 4-methyloctanoate at a lower cost, by fewer steps, and in higher yield. More specifically, there is provided a method for producing ethyl 4-methyloctanoate comprising the steps of: reacting 1-chloro-2-methylhexane through malonic ester synthesis to obtain diethyl 2-methylhexylmalonate, and subjecting the diethyl 2-methylhexylmalonate to a Krapcho reaction to obtain ethyl 4-methyloctanoate.

3 Claims, No Drawings

METHOD FOR PRODUCING ETHYL 4-METHYLOCTANOATE

RELATED APPLICATION

The present application claims priority to Japanese Patent Application No. 2016-052500 filed Mar. 16, 2016, the disclosure of which is incorporated by reference in its entirety.

BACKGROUND OF THE INVENTION

1. Field of the Invention

The present invention relates to a method for producing ethyl 4-methyloctanoate, which is an aggregation pheromone substance of Coconut Rhinoceros Beetle (*Oryctes rhinoceros*), an insect pest of palm trees and others.

2. Description of the Related Art

Coconut Rhinoceros Beetle is an important insect pest of palm trees, pineapples, coconuts, sugarcane and others. It has markedly strong boring ability. The adults of this insect pest tunnel the shoot apex of such a plant and stay there with eating activity, so that the plant withers and dies at the time when the growing point was bored through by them and lost. This species is found over a wide area such as Southeast Asia, Hawaii, and Guam now. Although it brings enormous damage to plants belonging to the family Palmae, it cannot easily be controlled by insecticides and an effective control method has not yet been established. On the other hand, control with an aggregation pheromone substance has drawn attention and its use is expected.

It has been found that an aggregation pheromone substance of Coconut Rhinoceros Beetle is ethyl 4-methyloctanoate (R. H. Hallett et al., J. Chem. Ecol. 1995, 21(10), 1549-1570). Several synthesizing methods of this aggregation pheromone substance have been reported. For example, Gries et al. have reported that ethyl 4-methyloctanoate can be obtained by reacting a Grignard reagent prepared from magnesium and 2-chlorohexane with ethyl acrylate in the presence of tetrahydrofuran, hexamethylphosphoric triamide, trimethylchlorosilane and, as a catalyst, copper (I) cyanide (G. Gries et al., Z. Naturforsch. 1994, 49c, 363-366). Valentine et al. have also reported that ethyl 4-methyloctanoate can be obtained by successively carrying out the following four steps of: a Mannich reaction between 1-hexanal and a 37% aqueous formalin solution, a reduction reaction of the aldehyde, a Johnson-Claisen rearrangement reaction, and a hydrogenation reaction (Valentine et al., J. Agricultural and Food Chemistry. 2007, 55, 5050-5052).

SUMMARY OF THE INVENTION

However, in the synthesis by Gries et al., hexamethylphosphoric triamide suspected of being carcinogenic is used, and the production yield is as low as 56%. Further, it is not suited for industrial production, because a homocoupled by-product of the Grignard reagent has a boiling point very close to that of the target ethyl 4-methyloctanoate so that separation through distillation is made difficult. On the other hand, in the synthesis by Valentine et al., the high-concentration aqueous formalin solution is used so that formaldehyde vapor toxic to human bodies may be generated, thereby making the handling difficult. Further, the production yield is as low as 55% as a result of the four steps.

With the foregoing in view, the invention has been made. An object of the invention is to provide a method for producing high-purity ethyl 4-methyloctanoate at a low cost, by fewer steps, and in higher yield.

It has been found that ethyl 4-methyloctanoate can be obtained with a high purity and in high yield by malonic ester synthesis of 1-chloro-2-methylhexane which can be provided in a large amount at a low cost and then by a Krapcho reaction, leading to the completion of the invention.

In the invention, there is provided a method for producing ethyl 4-methyloctanoate comprising the steps of: reacting 1-chloro-2-methylhexane through malonic ester synthesis to obtain diethyl 2-methylhexylmalonate, and subjecting the diethyl 2-methylhexylmalonate to a Krapcho reaction to obtain ethyl 4-methyloctanoate.

According to the invention, high-purity ethyl 4-methyloctanoate can be produced at a low cost, by fewer steps and in higher yield.

DETAILED DESCRIPTION OF THE PREFERRED EMBODIMENTS

The starting material 1-chloro-2-methylhexane (1) can be prepared, for example, by a coupling reaction between commercially available 1-bromo-3-chloro-2-methylpropane and commercially available propylmagnesium chloride.

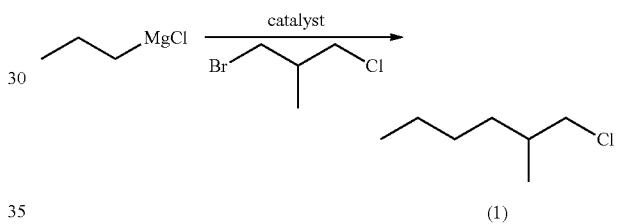

The 1-chloro-2-methylhexane (1) is reacted with diethyl malonate to obtain diethyl 2-methylhexylmalonate (2). This malonic ester synthesis can be carried out by reacting the 1-chloro-2-methylhexane (1) with diethyl malonate in a solvent in the presence of a base and a halide.

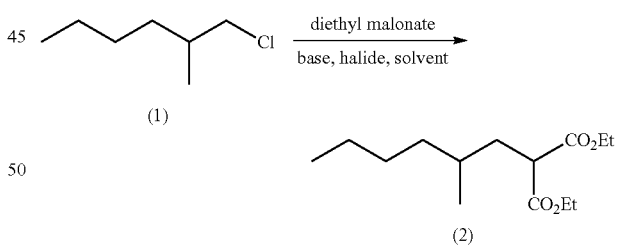

Examples of the base to be used for the malonic ester synthesis include carbonates such as lithium carbonate, sodium carbonate, calcium carbonate, potassium carbonate, cesium carbonate and barium carbonate; hydrides such as sodium hydride, potassium hydride and calcium hydride; alkoxides such as lithium methoxide, lithium ethoxide, lithium t-butoxide, lithium t-amyloxide, sodium methoxide, sodium ethoxide, sodium t-butoxide, sodium t-amyloxide, potassium methoxide, potassium ethoxide, potassium t-butoxide and potassium t-amyloxide; and metal amides such as lithium amide, lithium diisopropylamide, lithium hexamethyldisilazide, lithium dicyclohexylamide, sodium amide, sodium hexamethyldisilazide and potassium hexamethyldisilazide. From the standpoint of suppressing dialkylation and efficiently providing a monoalkylated body, carbonates such as lithium carbonate, sodium carbonate, calcium carbonate, potassium carbonate, cesium carbonate and barium carbonate are preferred. The base may be used singly or in combination of two or more. The base may be used in an amount of from 0.5 mol to 2.5 mol per mol of 1-chloro-2-methylhexane from the standpoint of reactivity.

Examples of the halide to be used for the malonic ester synthesis include sodium iodide, potassium iodide, sodium bromide and potassium bromide. From the standpoint of reactivity, iodides such as sodium iodide and potassium iodide are preferred. When a large amount of 1-bromo-2-methylhexane or 1-iodo-2-methylhexane having high reactivity is present in the system at the initial stage of the reaction, diethyl 2-methylhexylmalonate (2), which is a product of the malonic ester synthesis, is further reacted to yield a corresponding dialkylated body as a by-product. On the other hand, the by-product dialkylated body can be suppressed by making use of a marked difference in reactivity toward diethyl malonate between 1-chloro-2-methylhexane and 1-iodo-2-methylhexane, more specifically by gradually iodinating 1-chloro-2-methylhexane having lower reactivity, and at same time instantly reacting the resulting 1-iodo-2-methylhexane with diethyl malonate. The halide may be used singly or in combination of two or more. The halide may be used in an amount of preferably from 0.001 mol to 2.0 mol per mol of 1-chloro-2-methylhexane from the standpoint of reactivity.

Examples of the solvent to be used for the malonic ester synthesis include hydrocarbons such as toluene and hexane; ethers such as tetrahydrofuran and diethyl ether; and polar solvents such as N,N-dimethylformamide, N,N-dimethylacetamide, dimethyl sulfoxide and acetonitrile. From the standpoint of reactivity, N,N-dimethylacetamide is preferred. The solvent may be used singly or in a combination of two or more. The solvent may be used in an amount of from 300 g to 2000 g per mol of 1-chloro-2-methylhexane from the standpoint of reactivity.

The reaction temperature for the malonic ester synthesis is variable depending on the solvent to be used. It is preferably from 35° C. to 189° C. from the standpoint of reactivity.

The diethyl 2-methylhexylmalonate (2) thus obtained is subjected to a Krapcho reaction to produce ethyl 4-methyloctanoate (3). This Krapcho reaction can be carried out by heating the diethyl 2-methylhexylmalonate (2) in a solvent in the presence of a salt and water.

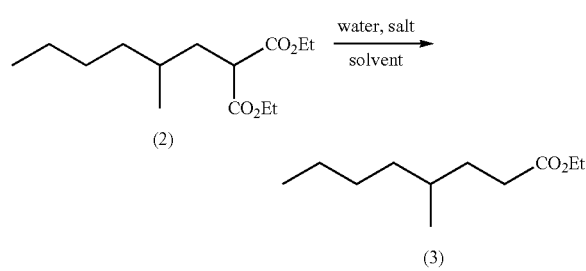

Examples of the salt to be used for the Krapcho reaction include lithium salts such as lithium chloride, lithium bromide and lithium iodide; sodium salts such as sodium fluoride, sodium chloride, sodium bromide, sodium iodide, sodium cyanide, sodium acetate, sodium nitrate, sodium dihydrogen phosphate, sodium hydrogen phosphate, disodium hydrogen phosphate, sodium carbonate, sodium sulfate and sodium hydrogen sulfate; potassium salts such as potassium chloride, potassium bromide, potassium iodide, potassium cyanide, potassium acetate, potassium nitrate, potassium dihydrogen phosphate, potassium hydrogen phosphate, dipotassium hydrogen phosphate, potassium carbonate, potassium sulfate and potassium hydrogen sulfate; and magnesium salts such as magnesium chloride. The salt may be used singly or in combination of two or more. The salt may be used in an amount of preferably from 1.0 mol to 5.0 mol per mol of diethyl 2-methylhexylmalonate from the standpoint of reactivity.

With regard to water to be used for the Krapcho reaction, the reaction proceeds even without water, but addition of water tends to increase the reaction rate. Water can be added in an amount of preferably from 1.0 mol to 5.0 mol per mol of diethyl 2-methylhexylmalonate from the standpoint of reactivity.

Examples of the solvent to be used for the Krapcho reaction include a polar solvent such as N,N-dimethylformamide, N,N-dimethylacetamide and dimethyl sulfoxide; a mixed solvent of the polar solvent and a hydrocarbon solvent such as toluene or hexane; and a mixed solvent of the polar solvent and an ether solvent such as tetrahydrofuran or diethyl ether. From the standpoint of reactivity, N,N-dimethylacetamide is preferred. The solvent may be used in an amount of preferably from 300 g to 2000 g per mol of diethyl 2-methylhexylmalonate from the standpoint of reactivity.

The temperature of the Krapcho reaction differs depending on the solvent to be used. It is preferably from 100° C. to 190° C. from the standpoint of reactivity.

The step of malonic ester synthesis and the step of Krapcho reaction may be carried out separately so that the product (2) of the malonic ester synthesis may be isolated and then subjected to the Krapcho reaction. However, it is preferred to carry out, subsequently to the step of malonic ester synthesis, the step of Krapcho reaction in situ, in other words, to successively carry out the malonic ester synthesis reaction and the Krapcho reaction as one pot synthesis. Time spent for work-up, concentration, re-charging into a reactor and others can be reduced largely by successively carrying out the reactions. Further, the solvent used in the malonic ester synthesis can be used again in the Krapcho reaction and a salt formed as a by-product in the malonic ester synthesis can be used in the Krapcho reaction, so that the number of reagents necessary for the reactions can be reduced largely and an amount of waste decreases, thereby leading to reduction of a burden to the environment.

EXAMPLES

The invention will hereinafter be described specifically by Examples. It should not be construed that the invention is limited to or by Examples.

Example 1

Production of diethyl 2-methylhexylmalonate

Sodium ethoxide (93.57 g, 1.38 mol), potassium iodide (1.83 g, 0.011 mol), N,N-dimethylacetamide (770 g) and tetrahydrofuran (330 g) were placed in a reactor at room temperature, and stirred at 25° C. for 30 minutes. After stirring, diethyl malonate (220.23 g, 1.38 mol) was dropwise added thereto at 60° C. or less, and the resulting mixture was stirred at 70° C. for 1.5 hours. Then 1-chloro-2-methylhexane (148.12 g, 1.10 mol) was dropwise added thereto at 70° C. The resulting mixture was then refluxed at 89° C. with stirring for 35 hours. After the reaction mixture was cooled to 50° C. or less, hexane (220 g) and water (880 g) were added to the reaction mixture to terminate the reaction. The reaction mixture was separated into organic and water phases. The organic phase separated from the water phase was subjected to addition of water (880 g), and then separated again. The organic phase was concentrated under reduced pressure to remove the hexane. The residue was distilled under reduced pressure to obtain diethyl 2-methylhexylmalonate (206.16 g, 0.798 mol) in yield of 72.6%.

[Nuclear magnetic resonance spectrum] $^1$H-NMR (500 MHz, CDCl$_3$): δ=0.86 (3H, t, J=7.3 Hz), 0.87 (3H, d, J=6.5 Hz), 1.09-1.16 (1H, m), 1.19-1.31 (5H, m), 1.24 (3H, t, J=7.3 Hz), 1.25 (3H, t, J=7.3 Hz), 1.34-1.43 (1H, m), 1.65 (1H, ddd, 6.9, 8.3, 14.0 Hz), 1.93 (1H, ddd, 5.3, 8.6, 14.0 Hz), 3.41 (1H, dd, J=6.9, 8.8 Hz), 4.17 (2H, q, J=7.3 Hz), 4.17 (2H, q, J=7.3 Hz); $^{13}$C-NMR (500 MHz, CDCl$_3$): δ=14.02, 14.02, 14.04, 19.21, 22.79, 28.92, 30.74, 35.78, 36.36, 50.09, 61.18, 61.23, 169.65, 169.83

[Mass spectrum] EI-Mass spectrum (70 eV): m/z 259 (M$^+$+1), 213, 174, 160, 133, 29

[Infrared absorption spectrum] (NaCl): ν=2959, 2931, 1752, 1733, 1465, 1369, 1241, 1177, 1151, 1033

Example 2

Production of diethyl 2-methylhexylmalonate

Potassium t-butoxide (694.30 g, 6.19 mol), potassium iodide (164.35 g, 0.99 mol), N,N-dimethylacetamide (3465 g) and tetrahydrofuran (1485 g) were placed in a reactor at room temperature, and stirred at 25° C. for 30 minutes. After stirring, diethyl malonate (991.05 g, 6.19 mol) was dropwise added thereto at 60° C. or less and the resulting mixture was stirred at 70° C. for 30 minutes. Then 1-chloro-2-methylhexane (666.52 g, 4.95 mol) was dropwise added thereto at 90° C. or less. After completion of the dropwise addition, the resulting mixture was refluxed at 92° C. with stirring for 11 hours. After the reaction mixture was cooled to 50° C. or less, hexane (1485 g) and water (3960 g) were added to the reaction mixture to terminate the reaction. The reaction mixture was separated into organic and water phases. The organic phase separated from the water phase was subjected to addition of water (3960 g), and then separated again. The organic phase was concentrated under reduced pressure to remove the hexane. The residue was distilled under reduced pressure to obtain diethyl 2-methylhexylmalonate (906.81 g, 3.51 mol) in yield of 70.9%.

[Nuclear magnetic resonance spectrum] H-NMR (500 MHz, CDCl$_3$): δ=0.86 (3H, t, J=7.3 Hz), 0.87 (3H, d, J=6.5 Hz), 1.09-1.16 (1H, m), 1.19-1.31 (5H, m), 1.24 (3H, t, J=7.3 Hz), 1.25 (3H, t, J=7.3 Hz), 1.34-1.43 (1H, m), 1.65 (1H, ddd, 6.9, 8.3, 14.0 Hz), 1.93 (1H, ddd, 5.3, 8.6, 14.0 Hz), 3.41 (1H, dd, J=6.9, 8.8 Hz), 4.17 (2H, q, J=7.3 Hz), 4.17 (2H, q, J=7.3 Hz); $^{13}$C-NMR (500 MHz, CDCl$_3$): δ=14.02, 14.02, 14.04, 19.21, 22.79, 28.92, 30.74, 35.78, 36.36, 50.09, 61.18, 61.23, 169.65, 169.83

[Mass spectrum] EI-Mass spectrum (70 eV): m/z 259 (M$^+$+1), 213, 174, 160, 133, 29

[Infrared absorption spectrum] (NaCl): ν=2959, 2931, 1752, 1733, 1465, 1369, 1241, 1177, 1151, 1033

Example 3

Production of diethyl 2-methylhexylmalonate

Potassium carbonate (345.53 g, 2.50 mol), potassium iodide (3.32 g, 0.02 mol), N,N-dimethylacetamide (1400 g), diethyl malonate (480.51 g, 3.00 mol) and 1-chloro-2-methylhexane (269.30 g, 2.00 mol) were placed in a reactor at room temperature, and heated to 130° C. After the temperature reached 130° C., the resulting mixture was stirred for 7 hours. After the reaction mixture was cooled to 50° C. or less, hexane (400 g) and water (1600 g) were added to the reaction mixture to terminate the reaction. The reaction mixture was separated into organic and water phases. The organic phase separated from the water phase was subjected to addition of water (400 g), and then separated again. The organic phase was concentrated under reduced pressure to remove the hexane. The residue was distilled under reduced pressure to obtain diethyl 2-methylhexylmalonate (436.61 g, 1.69 mol) in yield of 84.4%.

[Nuclear magnetic resonance spectrum] $^1$H-NMR (500 MHz, CDCl$_3$): δ=0.86 (3H, t, J=7.3 Hz), 0.87 (3H, d, J=6.5 Hz), 1.09-1.16 (1H, m), 1.19-1.31 (5H, m), 1.24 (3H, t, J=7.3 Hz), 1.25 (3H, t, J=7.3 Hz), 1.34-1.43 (1H, m), 1.65 (1H, ddd, 6.9, 8.3, 14.0 Hz), 1.93 (1H, ddd, 5.3, 8.6, 14.0 Hz), 3.41 (1H, dd, J=6.9, 8.8 Hz), 4.17 (2H, q, J=7.3 Hz), 4.17 (2H, q, J=7.3 Hz); $^{13}$C-NMR (500 MHz, CDCl$_3$): δ=14.02, 14.02, 14.04, 19.21, 22.79, 28.92, 30.74, 35.78, 36.36, 50.09, 61.18, 61.23, 169.65, 169.83

[Mass spectrum] EI-Mass spectrum (70 eV): m/z 259 (M$^+$+1), 213, 174, 160, 133, 29

[Infrared absorption spectrum] (NaCl): ν=2959, 2931, 1752, 1733, 1465, 1369, 1241, 1177, 1151, 1033

Example 4

Production of diethyl 2-methylhexylmalonate

Potassium carbonate (6.91 g, 0.050 mol), sodium iodide (0.060 g, 0.4 mmol), N,N-dimethylacetamide (28 g), diethyl malonate (9.61 g, 0.06 mol) and 1-chloro-2-methylhexane (5.39 g, 0.040 mol) were placed in a reactor at room temperature, and heated to 130° C. After the temperature reached 130° C., the resulting mixture was stirred for 10 hours. After the reaction mixture was cooled to 50° C. or less, hexane (8 g) and water (32 g) were added to the reaction mixture to terminate the reaction. The reaction mixture was separated into organic and water phases. The organic phase separated from the water phase was subjected to addition of water (8 g), and then separated again. The organic phase was concentrated under reduced pressure to remove the hexane. The residue was purified by silica gel column chromatography to obtain diethyl 2-methylhexylmalonate (9.22 g, 0.0357 mol) in yield of 89.3%.

[Nuclear magnetic resonance spectrum] $^1$H-NMR (500 MHz, CDCl$_3$): δ=0.86 (3H, t, J=7.3 Hz), 0.87 (3H, d, J=6.5 Hz), 1.09-1.16 (1H, m), 1.19-1.31 (5H, m), 1.24 (3H, t, J=7.3 Hz), 1.25 (3H, t, J=7.3 Hz), 1.34-1.43 (1H, m), 1.65 (1H, ddd, 6.9, 8.3, 14.0 Hz), 1.93 (1H, ddd, 5.3, 8.6, 14.0 Hz), 3.41 (1H, dd, J=6.9, 8.8 Hz), 4.17 (2H, q, J=7.3 Hz), 4.17 (2H, q, J=7.3 Hz); $^{13}$C-NMR (500 MHz, CDCl$_3$): δ=14.02, 14.02, 14.04, 19.21, 22.79, 28.92, 30.74, 35.78, 36.36, 50.09, 61.18, 61.23, 169.65, 169.83

[Mass spectrum] EI-Mass spectrum (70 eV): m/z 259 (M$^+$+1), 213, 174, 160, 133, 29

[Infrared absorption spectrum] (NaCl): ν=2959, 2931, 1752, 1733, 1465, 1369, 1241, 1177, 1151, 1033

Example 5

Production of diethyl 2-methylhexylmalonate

Sodium carbonate (5.30 g, 0.050 mol), potassium iodide (0.066 g, 0.4 mmol), N,N-dimethylacetamide (28 g), diethyl malonate (9.61 g, 0.06 mol) and 1-chloro-2-methylhexane (5.39 g, 0.040 mol) were placed in a reactor at room temperature, and heated to 130° C. After the temperature reached 130° C., the resulting mixture was stirred for 22 hours. After the reaction mixture was cooled to 50° C. or less, hexane (8 g) and water (32 g) were added to the reaction mixture to terminate the reaction. The reaction mixture was separated into organic and water phases. The organic phase separated from the water phase was subjected to addition of water (8 g), and then separated again. The organic phase was concentrated under reduced pressure to remove the hexane. The residue was purified by silica gel column chromatography to obtain diethyl 2-methylhexyl-malonate (7.78 g, 0.0301 mol) in yield of 75.3%.

[Nuclear magnetic resonance spectrum] $^1$H-NMR (500 MHz, CDCl$_3$): δ=0.86 (3H, t, J=7.3 Hz), 0.87 (3H, d, J=6.5 Hz), 1.09-1.16 (1H, m), 1.19-1.31 (5H, m), 1.24 (3H, t, J=7.3 Hz), 1.25 (3H, t, J=7.3 Hz), 1.34-1.43 (1H,m), 1.65 (1H, ddd, 6.9, 8.3, 14.0 Hz), 1.93 (1H, ddd, 5.3, 8.6, 14.0 Hz), 3.41 (1H, dd, J=6.9, 8.8 Hz), 4.17 (2H, q, J=7.3 Hz), 4.17 (2H, q, J=7.3 Hz); $^{13}$C-NMR (500 MHz, CDCl$_3$): δ=14.02, 14.02, 14.04, 19.21, 22.79, 28.92, 30.74, 35.78, 36.36, 50.09, 61.18, 61.23, 169.65, 169.83

[Mass spectrum] EI-Mass spectrum (70 eV): m/z 259 (M$^+$+1), 213, 174, 160, 133, 29

[Infrared absorption spectrum] (NaCl): ν=2959, 2931, 1752, 1733, 1465, 1369, 1241, 1177, 1151, 1033

Example 6

Production of ethyl 4-methyloctanoate

Cesium carbonate (16.29 g, 0.050 mol), potassium iodide (0.066 g, 0.4 mmol), N,N-dimethylacetamide (56 g), diethyl malonate (9.61 g, 0.06 mol) and 1-chloro-2-methylhexane (5.39 g, 0.040 mol) were placed in a reactor at room temperature, and heated to 130° C. After the temperature reached 130° C., the resulting mixture was stirred for 8 hours. After the reaction mixture was cooled to 50° C. or less, hexane (8 g) and water (32 g) were added to the reaction mixture to terminate the reaction. The reaction mixture was separated into organic and water phases. The organic phase separated from the water phase was subjected to addition of water (8 g), and then separated again. The organic phase was concentrated under reduced pressure to remove the hexane. The residue was purified by silica gel column chromatography to obtain, as an intermediate, diethyl 2-methylhexylmalonate (4.37 g, 0.0169 mol) in yield of 42.3% and, as a final product, ethyl 4-methyloctanoate (3.10 g, 0.0166 mol) in yield of 41.66%. The isolated diethyl 2-methylhexylmalonate (4.37 g, 0.0169 mol), sodium chloride (1.05 g, 0.018 mol), water (0.59 g, 0.032 mol) and N,N-dimethylacetamide (15.16 g) were added to the reactor at room temperature and the resulting mixture was refluxed at 139° C. After the reflux was started, the mixture was stirred under reflux conditions for 13.5 hours. After the reaction mixture was cooled to 50° C. or less, hexane (7.22 g) and water (12.03 g) were added to the reaction mixture to terminate the reaction. The reaction mixture was separated into organic and water phases. The organic phase separated from the water phase was subjected to addition of water (12.03 g), and then separated again. The organic phase was concentrated under reduced pressure to remove the hexane. The residue was purified by silica gel column chromatography to obtain ethyl 4-methyloctanoate (3.05 g, 0.0164 mol). As a result of the two steps, ethyl 4-methyloctanoate (6.15 g, 0.033 mol) was obtained in yield of 82.5%.

[Nuclear magnetic resonance spectrum] $^1$H-NMR (500 MHz, CDCl$_3$): δ=0.86 (3H, t, J=6.5 Hz), 0.87 (3H, t, J=6.9 Hz), 1.08-1.15 (1H, m), 1.20-1.32 (6H, m), 1.24 (2H, t, J=7.3 Hz), 1.36-1.46 (2H, m), 1.60-1.69 (1H, m), 2.21-2.34 (2H, m), 4.11 (2H, q, J=6.9 Hz); $^{13}$C-NMR (500 MHz, CDCl$_3$): δ=14.06, 14.21, 19.26, 22.91, 29.13, 31.90, 32.17, 32.35, 36.31, 60.12, 174.12

[Mass spectrum] EI-Mass spectrum (70 eV): m/z 186 (M$^+$), 157, 141, 101, 88, 73, 29

[Infrared absorption spectrum] (NaCl): ν=2958, 2928, 1738, 1463, 1377, 1251, 1177, 1109, 1037

Example 7

Production of ethyl 4-methyloctanoate

Diethyl 2-methylhexylmalonate (401.74 g, 1.56 mol), sodium chloride (97.22 g, 1.66 mol), water (54.04 g, 3.00 mol) and N,N-dimethylacetamide (1399.26 g) were placed in a reactor at room temperature, and refluxed at 139° C. After the reflux was started, the resulting mixture was stirred under reflux conditions for 13.5 hours. After the reaction mixture was cooled to 50° C. or less, hexane (666.43 g) and water (1110.71 g) were added to the reaction mixture to terminate the reaction. The reaction mixture was separated into organic and water phases. The organic phase separated from the water phase was subjected to addition of water (1110.71 g), and then separated again. The organic phase was concentrated under reduced pressure to remove the hexane. The residue was distilled under reduced pressure to obtain ethyl 4-methyloctanoate (561.57 g, 3.01 mol) in yield of 96.9%.

[Nuclear magnetic resonance spectrum] $^1$H-NMR (500 MHz, CDCl$_3$): δ=0.86 (3H, t, J=6.5 Hz), 0.87 (3H, t, J=6.9 Hz), 1.08-1.15 (1H, m), 1.20-1.32 (6H, m), 1.24 (2H, t, J=7.3 Hz), 1.36-1.46 (2H, m), 1.60-1.69 (1H, m), 2.21-2.34 (2H, m), 4.11 (2H, q, J=6.9 Hz); $^{13}$C-NMR (500 MHz, CDCl$_3$): δ=14.06, 14.21, 19.26, 22.91, 29.13, 31.90, 32.17, 32.35, 36.31, 60.12, 174.12

[Mass spectrum] EI-Mass spectrum (70 eV): m/z 186 (M$^+$), 157, 141, 101, 88, 73, 29

[Infrared absorption spectrum] (NaCl): ν=2958, 2928, 1738, 1463, 1377, 1251, 1177, 1109, 1037

Example 8

Production of ethyl 4-methyloctanoate

Potassium carbonate (552.84 g, 4.00 mol), potassium iodide (6.64 g, 0.04 mol), N,N-dimethylacetamide (2800 g), diethyl malonate (961.02 g, 6.00 mol) and 1-chloro-2-methylhexane (538.60 g, 4.00 mol) were placed in a reactor at room temperature, and heated to 130° C. After the temperature reached 130° C., the resulting mixture was stirred for 9 hours. Then, while the mixture was kept at 130° C., the mixture was subjected to addition of water (139.04 g, 7.72 mol). The resulting mixture was refluxed at 116° C. with stirring for 12 hours. After the reaction mixture was cooled to 50° C. or less, hexane (800 g) and water (3200 g) were added to the reaction mixture to terminate the reaction. The reaction mixture was separated into organic and water phases. The organic phase separated from the water phase was subjected to addition of water (800 g), and then separated again. The organic phase was concentrated under reduced pressure to remove the hexane. The residue was distilled under reduced pressure to obtain ethyl 4-methyl-octanoate (594.34 g, 3.19 mol) in two-step yield of 79.8%.

[Nuclear magnetic resonance spectrum] $^1$H-NMR (500 MHz, CDCl$_3$): δ=0.86 (3H, t, J=6.5 Hz), 0.87 (3H, t, J=6.9 Hz), 1.08-1.15 (1H, m), 1.20-1.32 (6H, m), 1.24 (2H, t, J=7.3 Hz), 1.36-1.46 (2H, m), 1.60-1.69 (1H, m), 2.21-2.34 (2H, m), 4.11 (2H, q, J=6.9 Hz); $^{13}$C-NMR (500 MHz, CDCl$_3$): δ=14.06, 14.21, 19.26, 22.91, 29.13, 31.90, 32.17, 32.35, 36.31, 60.12, 174.12

[Mass spectrum] EI-Mass spectrum (70 eV): m/z 186 (M$^+$), 157, 141, 101, 88, 73, 29

[Infrared absorption spectrum] (NaCl): ν=2958, 2928, 1738, 1463, 1377, 1251, 1177, 1109, 1037

The invention claimed is:

1. A method for producing ethyl 4-methyloctanoate comprising the steps of:
    reacting 1-chloro-2-methylhexane with diethyl malonate in the presence of a halide selected from the group consisting of sodium iodide, potassium iodide, sodium bromide and potassium bromide to obtain diethyl 2-methylhexylmalonate; and
    subjecting the diethyl 2-methylhexylmalonate to a Krapcho reaction to obtain ethyl 4-methyloctanoate.

2. The method for producing ethyl 4-methyloctanoate according to claim 1, wherein the Krapcho reaction is carried out in situ, subsequently to the step of reacting 1-chloro-2-methylhexane.

3. The method for producing ethyl 4-methyloctanoate according to claim 1, wherein the halide is present in an amount of 0.001 mol to 2.0 mol per mol of the 1-chloro-2-methylhexane.

\* \* \* \* \*